United States Patent [19]
Anderson et al.

[11] Patent Number: 5,217,693
[45] Date of Patent: Jun. 8, 1993

[54] EMBRYO WASHING APPARATUS AND PROCESS

[76] Inventors: Mark Anderson, R.R. 2, Elmwood, Wis. 54740; James Griffin, 10015 Green St., Hebron, Ill. 60034

[21] Appl. No.: 529,280

[22] Filed: May 29, 1990

[51] Int. Cl.⁵ .............................................. G01N 1/10
[52] U.S. Cl. ................................. 422/100; 422/101; 422/103; 73/864.73; 73/864.01; 436/178; 436/180
[58] Field of Search ............... 422/100, 101, 103, 58; 73/864.73, 864.01; 436/177, 178, 180

[56] References Cited
U.S. PATENT DOCUMENTS

| | | | |
|---|---|---|---|
| 2,376,231 | 5/1945 | Cohn | 422/100 X |
| 2,423,173 | 7/1947 | Brady et al. | 422/100 X |
| 3,768,978 | 10/1973 | Grubb et al. | 422/100 X |
| 3,783,696 | 1/1974 | Coleman | 422/100 X |
| 3,864,979 | 2/1975 | Ayres | 422/100 X |
| 4,507,955 | 4/1985 | Haase | 73/864.01 |

Primary Examiner—Lynn M. Kummert
Attorney, Agent, or Firm—Edward H. Loveman

[57] ABSTRACT

This invention concerns apparatus and a method for preparing an embryo for cryogenic storage, and for thawing thereof prior to implantation. The apparatus employs a washing tube containing a microporous filter dividing the tube into two chambers between opposite open ends. A tubular coupling member is attachable to either end of the tube. A liquid driving device which may be an aspirator, drives holding, washing, and storing liquid through the tube while the filter retains the embryo in a washing chamber. A storage straw can be attached to the coupling member to receive by aspiration the storing liquid containing the embryo. The straw contains a movable plug or wick at one end to force the storing liquid and embryo out of the storage straw into the washing chamber, after the storing liquid is thawed.

4 Claims, 3 Drawing Sheets

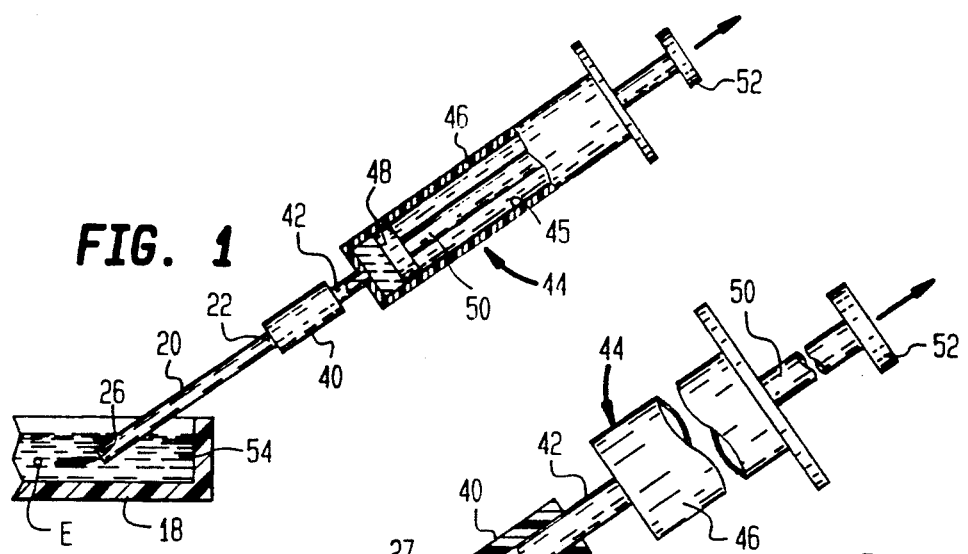
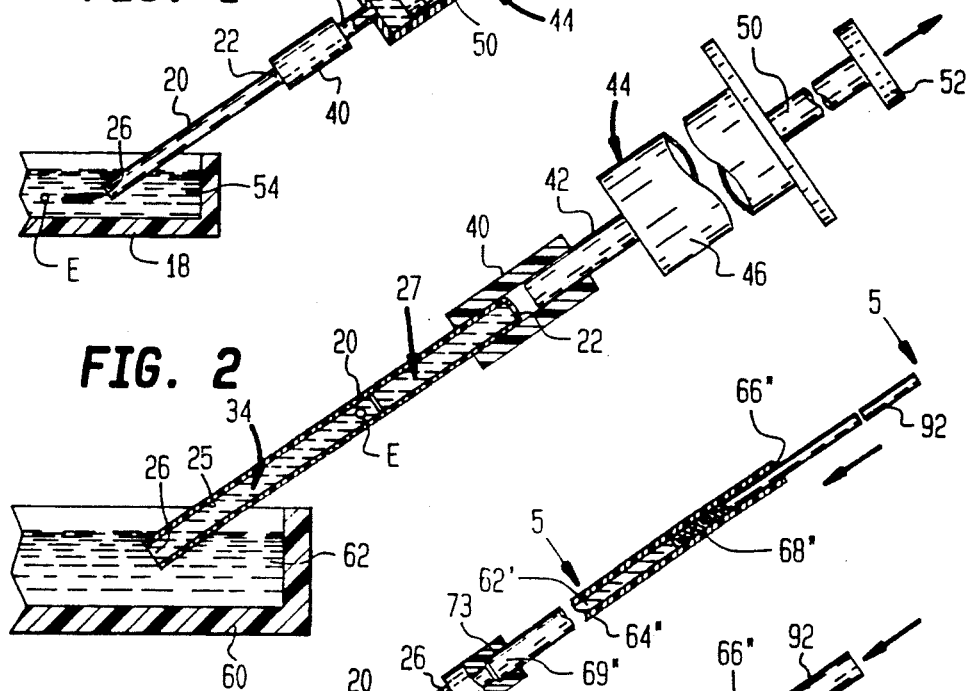
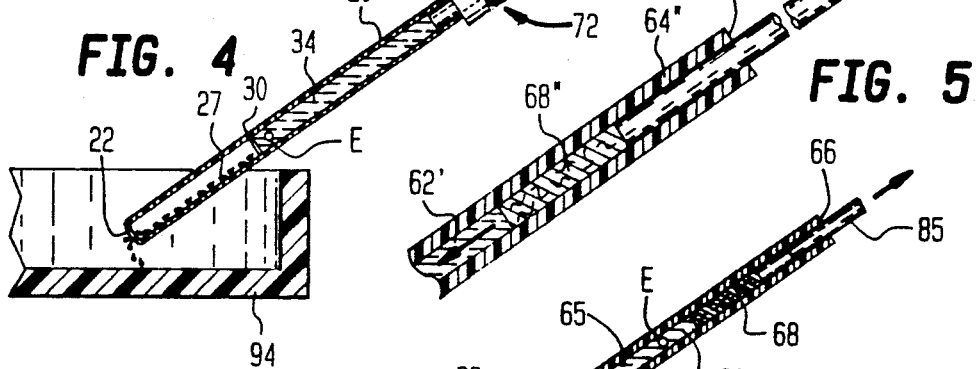
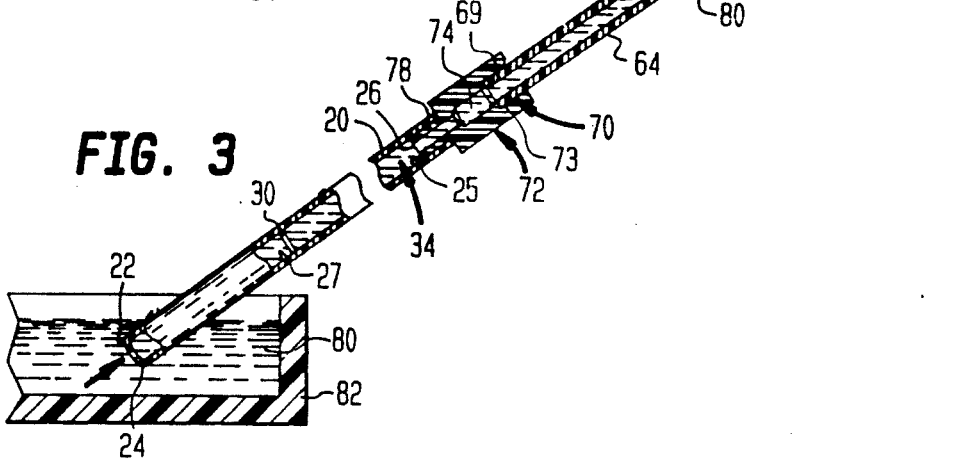

5,217,693

EMBRYO WASHING APPARATUS AND PROCESS

BACKGROUND OF THE INVENTION

1. Field of the Invention

This invention relates to apparatus and process for washing embryos before freezing for preservation and storage, and after thawing from a frozen state prior to implantation into a human or animal recipient; and more particularly, the invention concerns apparatus which facilitates washing an embryo and then transferring it to a storage straw or tube; and apparatus for transferring a thawed embryo from a storage straw or tube to a washing chamber where the embryo is washed.

2. Description of the Prior Art

Heretofore it has been necessary to transfer an embryo through containers of different media to effect ;washing and freezing or thawing and washing. It is very difficult to prevent contamination and damage to the embryo when it must be repeatedly handled during processing. The prior processing procedures have been very complex, time consuming, and laborious; and require skilled professional personnel to perform them. Nevertheless loss of or damage to the embryo is often experienced.

SUMMARY OF THE INVENTION

It is a principal object of the present invention to provide relatively simple, disposable apparatus and a method which minimizes the number of steps required to process an embryo safely through washing and transfer to storage for freezing, and to process an embryo after thawing through a washing procedure.

According to the invention, there is provided a plastic washing tube having a narrow internal bore across which is a microporous filter, disposed between opposite ends of the tube, to divide the tube into a washing chamber and a fluid transfer chamber. A rubber or plastic coupling nipple can be removably connected to one open end of the washing tube, and a syringe can be connected to the coupling nipple. The washing tube can then be disposed in an inclined position, and the lower open other end of the washing tube can be immersed in a first dish or vessel containing a holding fluid with an embryo to be retrieved, washed and frozen. The syringe will be operated to aspirate holding fluid containing the embryo into the washing chamber of the washing tube. Then the washing tube will be transferred to a second vessel containing washing fluid, with the washing tube still held in an inclined position. The syringe will be operated again to aspirate washing fluid through the washing chamber while the embryo remains in the washing chamber. Then the syringe and coupling nipple will be removed, and the washing tube containing the embryo will be turned end-to-end and again disposed in an inclined position. A tubular connector will be attached to the upper other end of the wash tube and the lower, open end of the washing tube will be immersed into a third vessel containing storing fluid. A storage straw or tube closed at one end by a porous plug or wick will have a free open end inserted into the tubular connector at the upper end of the washing tube, while the lower end of the washing tube is immersed in the storing fluid. A vacuum source will be applied to the upper end of the storage straw to aspirate the embryo and storing fluid into the storage straw while the lower end of the washing tube remains immersed in the storing fluid. The washing fluid is strained out of the storage straw by the porous plug while the storing fluid containing the embryo fills the storage straw. Then the plastic straw will be removed from the tubular connector and washing tube, and the storage tube will be inverted to a vertical position with the porous plug or wick at the bottom. The upper open end of the plastic straw will then be closed by heat sealing. The sealed straw containing the embryo and storing fluid can then be frozen and placed in cryogenic storage.

In a modification of the procedure described above, after the embryo is aspirated into the washing chamber from the first holding vessel, the syringe and coupling nipple will be removed and the inclined washing tube will be turned end-to-end to an inclined position. A tubular connector can then be attached to the open upper end of the washing tube and a straw or tube filled with washing fluid can be attached to the tubular connector. The washing straw will have a porous plug at its upper free end The washing fluid can be expelled from the washing straw into the washing chamber of the washing tube by pushing the plug along the inside of the straw, by means of a long narrow rod. After the washing straw is empty and the washing fluid has washed the embryo in the washing tube, the washing tube will be removed and replaced by a storage straw. Then the embryo will be aspirated with storing fluid into the storage straw as described above for subsequent freezing and storage.

In both procedures described above, the embryo is aspirated into the washing chamber of the washing tube and after washing it is aspirated into a storage straw or tube. At all times the embryo is protected from damage and contamination. It is transferred a minimum number of times. The apparatus employs simple plastic components which can be used by paraprofessional personnel, with a minimum expenditure of training time and effort, to achieve satisfactory embryo retrieval, washing, storage, and cryogenic preservation. The same type of washing apparatus may be used for washing a thawed embryo prior to implantation into a recipient.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 1 is a side view of apparatus embodying the invention shown in position for retrieving an embryo from a holding vessel, parts of the apparatus being broken away to show internal construction;

FIG. 2 is a side view on an enlarged scale showing the apparatus comprising washing tube and syringe arranged for washing a retrieved embryo, parts of the apparatus being broken away;

FIG. 3 is a view on the same scale as FIG. 2 showing the washing tube and storage straw connected and arranged to receive the embryo and storing liquid;

FIG. 4 is a side view of apparatus comprising washing tube and washing straw illustrating an alternate way of washing the retrieved embryo;

FIG. 5 is an enlarged portion of FIG. 4 taken along line 5—5;

DESCRIPTION OF THE PREFERRED EMBODIMENTS

Figure 6:
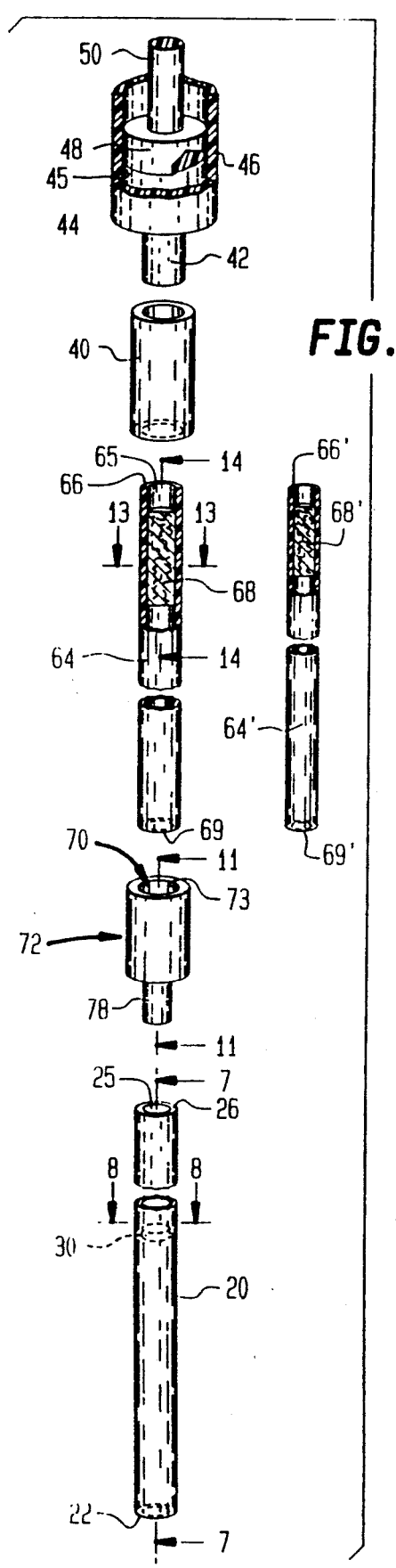
FIG. 6 is an enlarged exploded isometric view showing components of the apparatus according to the invention, parts being broken away to show internal construction.
Figure 7:
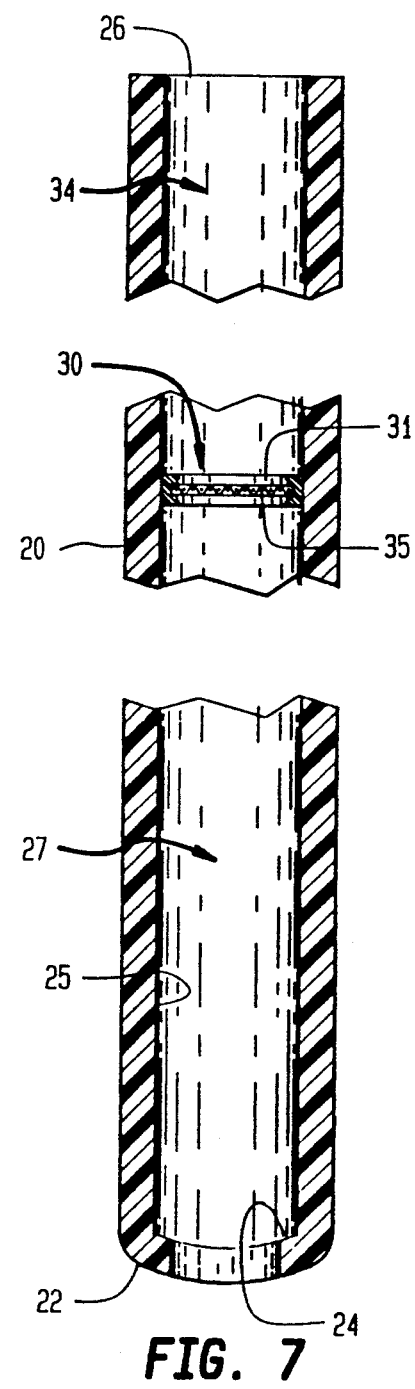
FIG. 7 is a further enlarged axial sectional view taken along line 7—7 of FIG. 6, through the washing tube, parts being broken away.
Figure 8:
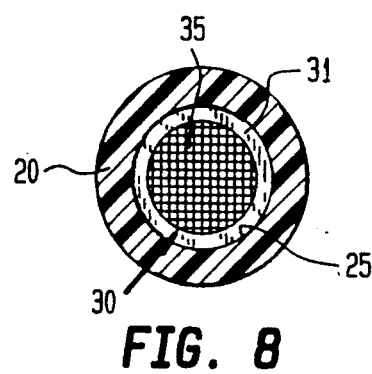
FIG. 8 is an enlarged cross sectional view taken along line 8—8 of FIG. 6.
Figure 11:
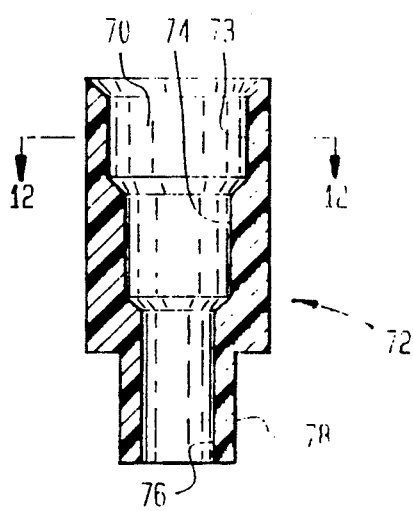
FIG. 11 is an axial cross sectional view taken along line 11—11 through the tubular connector 70 of FIG. 6.
Figure 12:
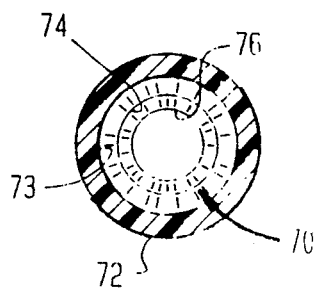
FIG. 12 is an enlarged cross sectional view taken along line 12—12 of FIG. 11.

Referring now to the drawings wherein like reference characters designate like or corresponding parts throughout, there is illustrated in FIG. 1 an assemblage of apparatus used to retrieve an embryo E from a holding vessel 18. The apparatus comprises a washing tube 20 shown in section and on enlarged scales; in FIGS. 2, 3, 4, 6, 7 and 8. The washing tube 20 is preferably made of polyvinyl chloride or other suitable plastic and is preferably about 8 centimeters long, about 4 millimeters in external diameter and about 3 millimeters in internal diameter. The tube 20 is open at opposite ends. One end 22 is rounded and formed with an internal annular bead 24 to restrict the rate of flow of a liquid through a bore 25 in the tube 20. The other end 26 of the tube 20 is annular and flat; see FIG. 7. Inside the tube 20 and extending diametrally across the bore 25 is a filter unit 30 (best shown in FIGS. 7-10) which is located between the tube ends 22 and 26 to define a washing chamber 34 between the filter unit 30 and the tube end 26. A fluid straining chamber 27 is located between the filter unit 30 and the beaded end 22. The filter unit 30 has an annular ring 31 with an internal groove 33 in which is set a circular microscreen 35 preferably made of polyethylene, 10-micron micromesh. The ring 31 can be rubber or plastic and it frictionally grips the inside of the tube 20. Chambers 34 and 27 are axially aligned with chamber 34 being slightly longer than chamber 27 as best shown in FIG. 2.

A tubular coupling nipple 40 is removably mounted on the beaded end 22 of the tube 20 as shown in FIG. 1. Removably attached to the coupling nipple 40 is a tubular end 42 of a manually operable syringe 44. The syringe 44 has a cylindrical chamber 45 in a cylindrical body 46. In the chamber 45 is an axially movable piston 48 secured to a piston rod 50 which terminates in a knob 52 outside the syringe 44.

In order to retrieve the embryo E immersed in a holding fluid 54 in the vessel 18, the tube 20 will be disposed in an inclined position with the flat end 26 of tube 20 immersed in the fluid 54 as indicated in FIG. 1. By retracting the piston rod 50 axially outward, the embryo E in the holding fluid 54 will be aspirated by suction into the washing chamber 34 as shown in FIG. 2.

Figure 14:
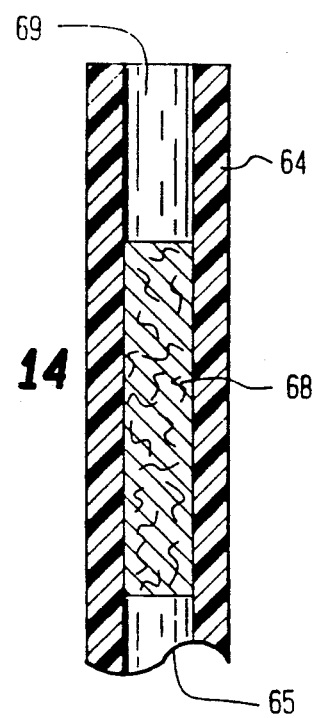
FIG. 14 is a fragmentary, enlarged axial sectional view taken along line 14—14 through the storage straw of FIG. 6.
Figure 13:
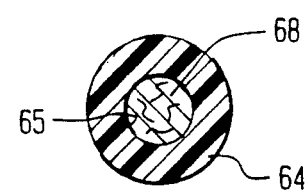
FIG. 13 is an enlarged cross sectional view taken along line 13—13 through the storage straw of FIG. 6.

In order to wash the embryo E in the washing chamber 34, the inclined washing tube 20 and the attached coupling nipple 40 and the syringe 44 will be transferred to a vessel 60 containing a washing fluid 62, as shown in FIG. 2. The flat end 26 of the tube 20 will be immersed in the washing fluid 62 and the piston rod 50 will be moved outwardly again to aspirate the washing fluid 62 into the tube 20, and into the syringe chamber 45. When sufficient washing fluid has passed through the filter unit 30, the embryo E will be ready for transfer to a storage tube or straw 64 shown in FIG. 3 and FIG. 6. The storage straw 64 is a plastic tube about 12 to 14 centimeters long with an axial bore 65. The bore 65 has a diameter of about 2 millimeters so that the tube has a capacity of about 0.5 cc. At one end 66 of the tube 64 is a cylindrical plug 68 comprising a wick made of cotton fibers which can be filled with a powdered glycerine; see FIGS. 13 and 14. The other open end 69 of the tube 64 will be inserted in an axial bore 70 of a tubular connector 72. The tubular connector 72 as best shown in FIGS. 3, 6, 11 and 12 has a bore section 73 of larger diameter, than inner bore section 74 which has a smaller diameter, and an end bore section 76 of smallest diameter. The free end 69 of the straw or tube 64 is inserted into the widest bore section 73. The connector 72 is formed with a short nipple 78 which fits snugly into the bore 25 in the washing tube 20 at the flat end 26. The washing tube 20 is shown turned 180° from the position illustrated in FIGS. 1 and 2, so that rounded end 22 is free and can be immersed into a storing liquid 80 in a vessel 82. The syringe 44 and the coupling nipple 40 are removed so that the embryo E in the washing chamber 34 may be aspirated along with the storing fluid 80 into the storage straw or tube 64 as shown in FIG. 3 upon application of a vacuum source 85, such as a suction pump, or syringe, to the outer end 66 of the storage tube 64. During the transfer of the storage fluid 80 to the storage tube 64, the washing fluid 62 is drained out through the porous plug or wick 68. Thereafter, the powder in the wick sets or gels to self seal the plug 68 at the end 66 of the storage tube 64. The storage tube 64 will be removed from the washing tube 20 after the embryo E is fully immersed in the storing fluid 80 as indicated in FIG. 3. The free open end 69 of the storage tube 64 will be heat sealed closed to prevent the storing fluid 80 from running out of the storage tube 64. The sealed storage tube 64 containing the embryo E and the storage liquid 80 can be frozen and put into cryogenic storage.

The storage tube 64 has an internal capacity of about 0.5 cc. If a storage tube of smaller capacity, such as 0.25 cc. is required, the narrow storage straw or tube 64' shown in FIG. 6 may be used. This straw 64' has a width of about 2 millimeters and a length of 12 to 14 centimeters. Inside the straw 64' at an end 66' is a cylindrical plug or wick 68'. An other open end 69' can be inserted into the inner narrower bore section 74 of the tubular connector 72. The straw 64' will be used like straw 64 as described above to receive the embryo and storage fluid 80 in the same way as indicated in FIG. 3.

Figure 15:
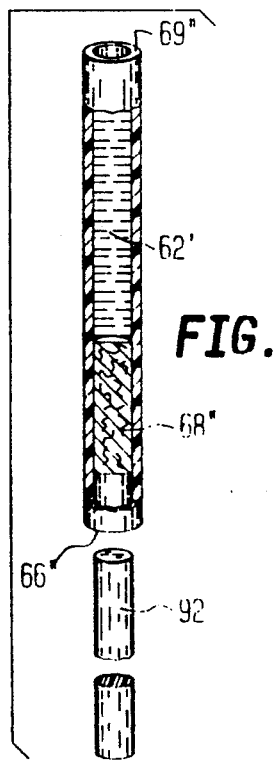
FIG. 15 is an isometric view of a washing straw containing washing fluid, parts of the straw being broken way, and with part of a push rod.
Figure 9:
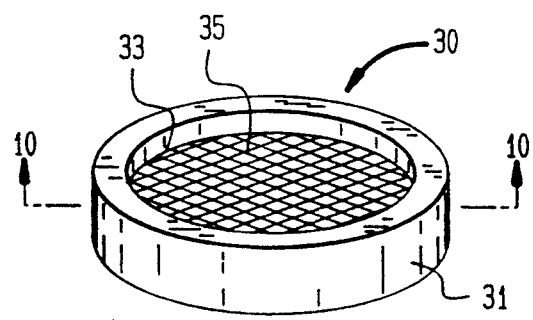
FIG. 9 is an enlarged isometric view of the filter unit per se.
Figure 10:
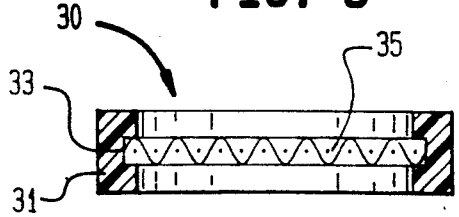
FIG. 10 is a cross section of the filter unit taken along line 10—10 of FIG. 9.

FIGS. 4 and 5 illustrate an arrangement of apparatus for performing an alternate way of washing the embryo E captured in washing compartment 34. A tubular washing straw 64" as shown in FIGS. 3, 4, and 15 is filled with a washing fluid 62'. The straw 64" is inverted and an open end 69" is inserted into the coupling connector 72 attached to the upper end 26 of the washing tube 20. A plug 68" closes the upper free end 66" of the inclined washing straw 64" which is axially aligned with the tube 20. A narrow push rod 92 may be inserted in the end 66" of the washing straw 64" to push the plug 68" axially downward as indicated in FIGS. 4 and 5 and force the washing fluid 62' into the washing chamber 34, from which the washing fluid 62' will drain through the filter unit 30 and the chamber 27 to discharge into a fluid collecting vessel 94. The apparatus thus provides two methods of performing the embryo washing step, either by aspirating washing fluid 62 upwardly by a syringe 44 or by forcing washing fluid 62' downward from the washing straw 64".

The storage straw 64 or 64' is closed at its open end 69 or 69' after it is filled with the storing fluid 80 in which is captured to embryo E. The closure, as pointed out above, is by heat sealing the open end 69 or 69'. Then the sealed storage straw 64 or 64' is frozen and stored cryogenically. When the embryo E is needed for implantation in a recipient, the storage straw 64 or 64' is thawed and the sealed end is cut off. The storage straw 64 or 64' is then inserted into the connector 72 attached to the upper end 26 of the axially inclined washing tube 20, in a manner similar to that shown in FIGS. 3 and 4. The push rod 92 can then be applied to the open end 66 or 66' and pushed axially downward to move the sealed plug 68 or 68' axially along the storage straw 64 or 64' forcing the embryo E and the storing liquid 80 out of the lower end 69 or 69' of the storage straw 64 or 64' into the washing chamber 34 of the washing tube 20. The embryo E will not pass the filter unit 30 so that the storing fluid 80 and the embryo E may be recovered after the empty storage straw 64 or 64' is removed, by either using the syringe 44 or by pouring the storing fluid 80 and the embryo E into another suitable receiving receptacle.

It will be noted that the apparatus can be used by unskilled or semiskilled personnel, since it is relatively simple in construction and operating procedures require no particular skill or training. Retrieval, washing, and ultimate recovery of the embryo are done under conditions where the embryo is never exposed to ambient air, since it is always immersed in a suitable fluid medium such as holding liquid 54, washing liquid 62 or storing liquid 80. The simple plastic parts of the apparatus can be discarded after a single usage.

It should be understood that the foregoing relateds only a preferred embodiment of the invention which has been by way of example only and that it is intended to cover all changes and modifications of the example of the invention herein chosen for the purpose of the disclosure, which do not consititute departures from the spirit and scope of the invention.

What is claimed is:

1. Apparatus for retrieving an embryo from a holding liquid, for washing the retrieved embryo in a washing liquid, and for storing the washed embryo in a storing liquid for freezing prior to thawing and implantation, comprising;
   an axially straight cylindrical washing tube having means defining an axial bore therein open at opposite ends of said tube, for application of suction thereto for drawing holding liquid containing an embryo into said bore;
   a microporous filter element in said bore extending thereacross and dividing said bore into axially aligned respective cylindrical washing chamber and straining chamber, said washing chamber extending between said filter element and one end of said bore at one end of said tube to retain a retrieved embryo therein in said holding and washing liquids, said straining chamber extending between said filter element and the other end of said bore to pass said holding and washing liquids through said filter element under suction applied to said other end of said bore;
   a straight hollow storage straw open at opposite ends of said straw;
   a tubular connector means having one end attachable to said one end of said tube and another end attachable to one end of said straw for axially aligning said straw with said tube; and
   a porous plug near the other end of said straw, whereby application of suction to said other end of said straw enables storing liquid containing a retrieved, washed embryo to be drawn into said straw for freezing and storage therein, prior to subsequent thawing for implantation of the thawed embryo.

2. Apparatus as claimed in claim 1, wherein said plug contains a settable self-sealing material to seal said other bore of said straw after suction is applied thereto to draw storing liquid therethrough; and wherein said straw is made of sealable material for closing said one end of said straw to enclose storage liquid and a washed embryo therein prior to and during freezing and storage.

3. Apparatus as claimed in claim 2, wherein said plug is axially movable in said straw after said one end thereof is cut off, to drive thawed storage liquid containing a thawed embryo out of said straw and into said washing chamber in said tube for washing the thawed embryo therein, prior to implantation of the embryo.

4. Apparatus as claimed in claim 1 wherein said tubular connector means comprises a cylindrical body with a first bore at one end, an inner bore section of smaller diameter than said first bore and an end bore at said other end of said body having a diameter smaller than said inner bore section, said one end of said straw fitting into said first bore, said tubular connector means having a short nipple at the other end thereof which is smaller in diameter than said cylindrical body, said nipple fitting snugly into said one end of said tube.

* * * * *